United States Patent [19]

Guillou et al.

[11] Patent Number: Plant 7,353

[45] Date of Patent: Oct. 9, 1990

[54] VARIETY OF GERANIUM NAMED RENEE

[75] Inventors: Jacques Guillou; Bernard Guillou; Maurice Guillou, all of Saint-Malo, France

[73] Assignee: Etablissement Guillou Feres Jacques, Bernard et Maruice, France

[21] Appl. No.: 359,835

[22] Filed: May 31, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Webb, Burden, Ziesenhelm & Webb

[57] ABSTRACT

A new ivy Geranium having many distinctive qualities that places it far ahead of the current market ivy varieties. The single red florets that accent the medium green foliage are less likely to show signs of petal burn. The plant habit and form is much more compact which creates a better cutting producer as well as creating a uniform plant. It stands up well outdoors in very high temperatures and is self-cleaning.

1 Drawing Sheet

BACKGROUND OF THE NEW PLANT

The present invention comprises a new and distinct cultivar of *Pelargonium×peltatum* known by the varietal name Renee (Oglevee Ltd. No. 7042, French No. 545 Guisuma). The new variety was discovered in a selective breeding program by Messrs. Jacques, Maurice and Bernard Guillou. The new variety is a selection from the crossing of Cocorico×No. 444. The new variety has a dark red color and keeps well in the sunlight as compared to its parentage.

The new cultivar was discovered in 1985 at 55 rue Godard, 35400 Saint-Malo, France, was first asexually reproduced by cuttings during 1986 and 1987 at Saint-Malo, France, and more recently has been repeatedly asexually reproduced by cuttings at Oglevee Ltd. in Connellsville, Pa. It has been found to retain its distinct characteristics through successive propagations.

The new cultivar, when grown in a glass greenhouse in Connellsville, Pa., using full light 60° F. night temperature, 68° F. day temperature, 71° F. vent temperature, and grown in a soilless media with constant fertilizer of 200–250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plants were started as rooted cuttings which were potted on Aug. 1, 1988 and flowered on Sept. 15, 1988. Three 10 cm pots were potted into a 26 cm hanging basket and maintained until Mar. 23, 1989 when the color readings were taken. The plant histories were taken of plants blossomed under full light in a greenhouse and color readings were taken indoors under 200–220 foot candles of cool white fluorescent light. Color references are primarily to the R.H.S. Colour Chart of The Royal Horticultural Society of London.

THE PLANT

Classification:
- *Botanical.*—*Pelargonium×peltatum.*
- *Commercial.*—Ivy Geranium (#7042) Renee.

Form: Cascading mound habit.

Height: 20–22 cm from media surface.

Growth: Free branching, upright growth with some cascading side growth.

Strength: Has an upright mound habit while outer branches cascade over the pot.

Foliage: Stalked leaf attachment; zone present but very faint.

Leaves:
- *Size.*—5.5–7.5 cm; fully expanded leaf.
- *Shape.*—Reniform, cordate base.
- *Margin.*—Pedately lobed.
- *Texture.*—Smooth; reflective.
- *Color.*—Green Group 137C.
- *Ribs and veins.*—Yellow-Green Group 146B.

Petioles: 4.5–6 cm in length.
- *Color.*—Yellow-Green Group 146B.

Stem:
- *Color.*—Yellow-Green Group 146C.
- *Internodes.*—2–6 cm in length.

THE BUD

Shape: Elliptical cluster; peduncle is bent allowing umbel to droop until maturity when the umbel and peduncle stand straight.

Size: 2–2.5 cm across.

INFLORESCENCE

Blooming habit: Continuous; upright; single floret.

Size: 9–10 cm across.

Borne: Florets on pedicel; pedicel on peduncle; umbel 4–6 cm above foliage canopy.

Florets:
- *Form.*—Flat to slightly cupped.
- *Color.*—Top: Red Group 44A; Venation of upper two petals: Red-Purple Group 59B. Bottom: Red Group 43A.
- *Petals.*—5 in number, separate, not united; margin entire.

*Floret size.*—5–5.5 cm across.

*Texture and appearance.*—Smooth; single floret containing 5 petals; appearance from a distance is a rich bright red with burgundy markings on upper petals.

Petaloids:

*Quantity.*—None present.

Pedicel: 3–3.5 cm in length.

*Color.*—Greyed-Purple Group 183B.

Peduncle: 11–13.5 cm in length.

*Color.*—Yellow-Green Group 146B.

Disease resistance: Not known.

Lasting quality: The single bloom and foliage seem more adapted to withstanding higher outdoor temperatures.

REPRODUCTIVE ORGANS

Stamens:

*Anthers.*—3 mm in length.

*Filaments.*—11–12 mm in length; white at base, pink at tip.

*Pollen.*—Golden brown.

Pistils:

*Number.*—One.

*Length.*—10–12 mm.

*Stigma.*—5 or 6 parted.

*Style.*—5–6 mm in length; white.

Ovaries: Superior; pubescent; pale green; 5 mm in length, 2–3 mm across.

Fruit: None observed.

GENERAL CHARACTERISTICS

This new ivy geranium has many distinctive qualities that places it far ahead of the current market ivy varieties. The single red florets that accent the medium green foliage are less likely to show signs of petal burn. The plant habit and form is much more compact which creates a better cutting producer as well as creating a uniform plant. It stands up well outdoors in very high temperatures and is self-cleaning.

When compared to Balcon Royal, the colors are similar but Renee has larger petals, larger flowers, more heat tolerance, larger ivy leaf and less trailing habit.

We claim:

1. A new and distinct variety of ivy Geranium plant as shown and described herein and characterized by single red florets that accent the medium green foliage, less likely to show signs of petal burn, the plant habit and form is very compact which creates a better cutting producer as well as creating a uniform plant, and it stands up well outdoors in very high temperatures and is self-cleaning.

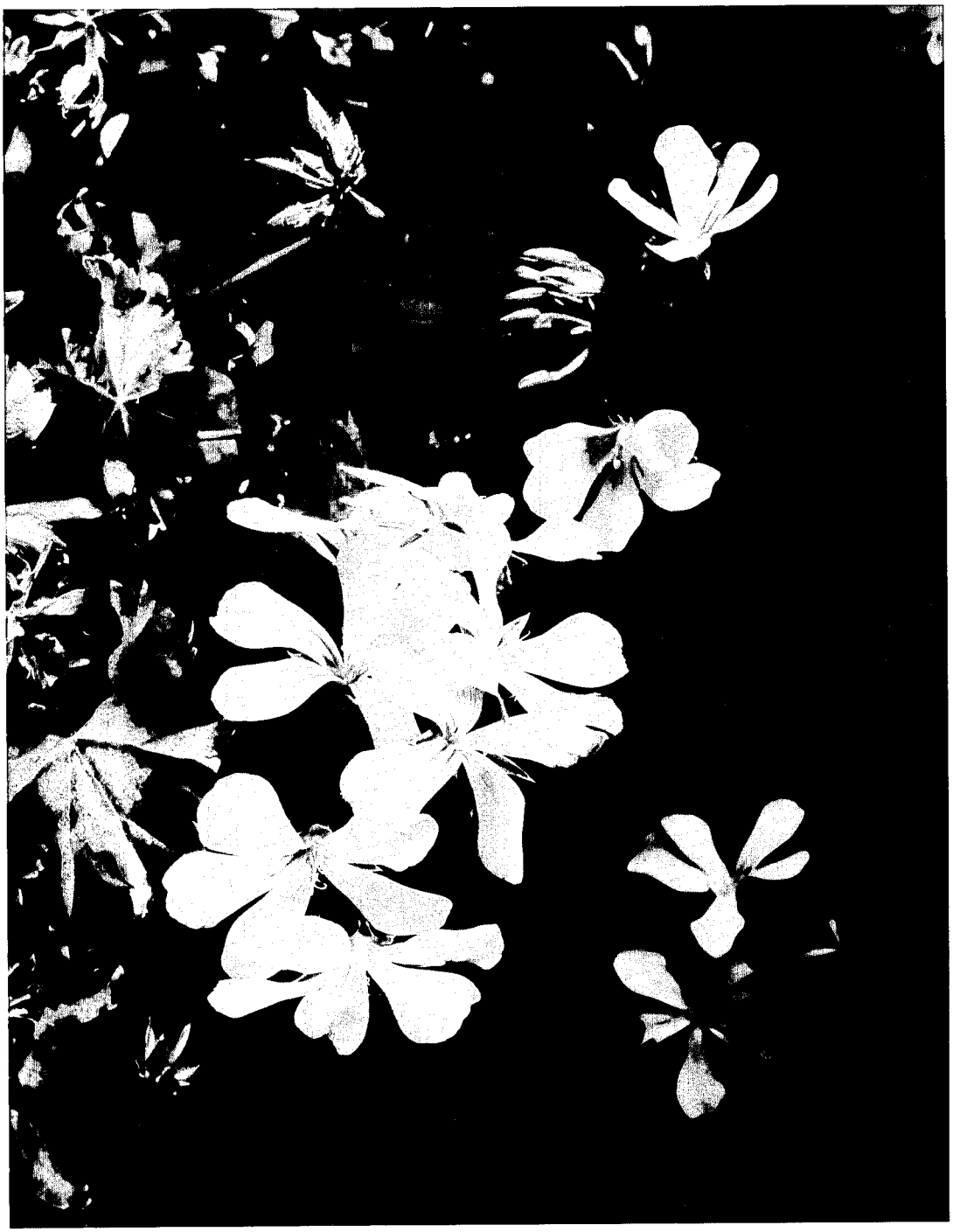

* * * * *